US00PP24722P3

(12) United States Plant Patent
Egger

(10) Patent No.: US PP24,722 P3
(45) Date of Patent: Jul. 29, 2014

(54) ***SEDUM* PLANT NAMED 'DYNOMITE'**

(50) Latin Name: ***Sedum* hybrid (syn. *Hylotelephium*)**
Varietal Denomination: Dynomite

(71) Applicant: Janet N. Egger, Wilsonville, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 130 days.

(21) Appl. No.: 13/694,126

(22) Filed: Oct. 30, 2012

(65) Prior Publication Data

US 2014/0123359 P1 May 1, 2014

(51) Int. Cl.
*A01H 5/00* (2006.01)

(52) U.S. Cl.
USPC ..... Plt./479

(58) Field of Classification Search
CPC ..... A01H 5/00; A01H 5/10; A01H 5/06; A01H 5/08; A01H 5/12; A01H 5/14; A01H 1/02; A01H 1/00; A01H 1/06
USPC ..... Plt./479
See application file for complete search history.

*Primary Examiner* — Susan McCormick Ewoldt
(74) *Attorney, Agent, or Firm* — Klarquist Sparkman, LLP

(57) ABSTRACT

A new and distinct hybrid of *Sedum* plant substantially as shown and described, characterized by burgundy red flowers in good size inflorescences, leaves with dark leaf margins and red tints, a very dwarf, clumping habit.

1 Drawing Sheet

Botanical denomination: *Sedum* hybrid (syn. *Hylotelephium*).

Variety designation: 'Dynomite'.

Parentage: *Sedum telephium* 2-7×*Sedum spectabile* 'Neon'.

BACKGROUND OF THE INVENTION

The present invention relates to a new and distinct cultivar of *Sedum* and given the cultivar name of 'Dynomite'. *Sedum* is in the family Crassulaceae. *Sedum* 'Dynomite' originated from a planned breeding program to produce hybrids with dark leaves, short stems and large inflorescences. *Sedum* 'Dynomite' originated from a cross between an unnamed, proprietary, an unpatented *Sedum telephium* 2-7 as the seed parent and *Sedum spectabile* 'Neon', unpatented, as the pollen parent.

Compared to the seed parent *Sedum telephium* 2-7, the new cultivar is has larger inflorescences with better flower color, and lighter colored leaves.

Compared to the pollen parent, *Sedum spectabile* 'Neon', the new cultivar, has leaves that have a red leaf edges and red tint in full sun rather than yellow green.

Compared to *Sedum* 'Birthday Party', (U.S. Plant Pat. No. 22,826), the new variety has a smaller and tighter habit and smaller inflorescences.

This new and unique *Sedum* is distinguished by:

1. burgundy red flowers in good size inflorescences,
2. leaves with dark leaf margins and red tints,
3. a very dwarf, clumping habit.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a two-year-old *Sedum* 'Dynomite' growing in the garden in August in Canby, Oreg.

DETAILED PLANT DESCRIPTION

The following is a detailed description of the new *Sedum* hybrid based on observations of three-year-old specimens grown in a garden in full sun under typical outdoor conditions in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The *Royal Horticultural Society Colour Chart, 5th* edition.

Plant:

*Type.*—Herbaceous perennial.
*Hardiness.*—USDA Zone 4 to 9.
*Size.*—20 cm tall from the ground to the top of the inflorescence and 27 cm wide.
*Habit.*—Erect, clumping.
*Vigor.*—Excellent.

Stem:

*Number.*—About 17.
*Size.*—8 cm long and 11 mm wide.
*Internode length.*—1 mm to 3 mm long.
*Color.*—Greyed Purple N187A.
*Texture.*—Succulent.
*Surface.*—Glabrous.

Leaf:

*Type.*—Simple.
*Arrangement.*—Opposite.
*Shape.*—Ovate to obovate.

*Apex.*—Acute.
*Base.*—Clasping.
*Venation.*—Pinnate.
*Margins.*—Undulate and sometimes serrate.
*Blade size.*—Grows to 3.5 cm long and 3.5 cm wide.
*Surface.*—Glabrous.
*Texture.*—Thick, spongy, succulent.
*Petiole.*—Leaves sessile.
*Leaf color.*—Topside closest to Green N137A, including vein, in full sun tinted Greyed Purple N187A, margin Greyed Purple N187A; bottom side Yellow Green 148C, including vein, top ⅓ tinted Greyed Purple 187A.

Inflorescence:
*Type.*—Terminal, corymbose.
*Number of flowers.*—About 400 per stem.
*Pedicels.*—2 mm to 5 mm long, 1 mm wide, glabrous, Greyed Brown N199A.
*Peduncle.*—Grows to 8 cm tall and 5 mm wide, between Greyed Purple 187B and Greyed Orange 177A, succulent, glabrous.
*Size.*—Grows to 6 cm tall and 7 cm wide.
*Bloom period.*—Late August through September in Canby, Oreg.

Flower bud:
*Size.*—3 mm wide, 7 mm deep.
*Description.*—Ovoid.
*Color.*—White NN155B at base blending to Red Purple 70A at tip.

Flower:
*Type.*—Complete, actinomorphic.
*Shape.*—Stellate.
*Size.*—5.5 mm deep and 5 mm wide.
*Color.*—Red Purple 71A.
*Corolla description.*—5 mm wide and 5 mm deep, 5 petals, each lanceolate, 6 mm long and 1.8 mm wide, margins entire, tip acuminate, glabrous on both sides, topside Red Purple 72B on top ¾ blending to Red Purple 69D on bottom ¼, bottom side Red Purple 72B on tip blending to Purple 75C at base.
*Calyx description.*—3 mm deep and 3 mm wide, stellate, 5 lobes, divided to the base, margins entire, tip acute, glabrous, Greyed Brown N199A on both sides.
*Stamen description.*—10 in number, 4 mm long, filaments 3.8 mm long, Red Purple 72B, anthers Greyed Purple N186A, pollen none, male sterile.
*Pistil description.*—5 separate prominent carpels, each 5 mm deep and 1 mm wide, Red Purple 71B, style 2 mm long, style and stigma Purple 71A.
*Fragrance.*—None.
*Lastingness.*—Each stem lasts up to a month.

Fruit:
*Type.*—Ventrally dehiscent follicle, erect, attenuate.
*Fertility.*—None.
*Color.*—Brown 200A.

Seed: No seed produced.

Disease and pest resistance or tolerance: Pest and disease resistance are typical for this type of *Sedum*. No known resistances.

I claim:

1. A new and distinct hybrid of *Sedum* plant as herein illustrated and described.

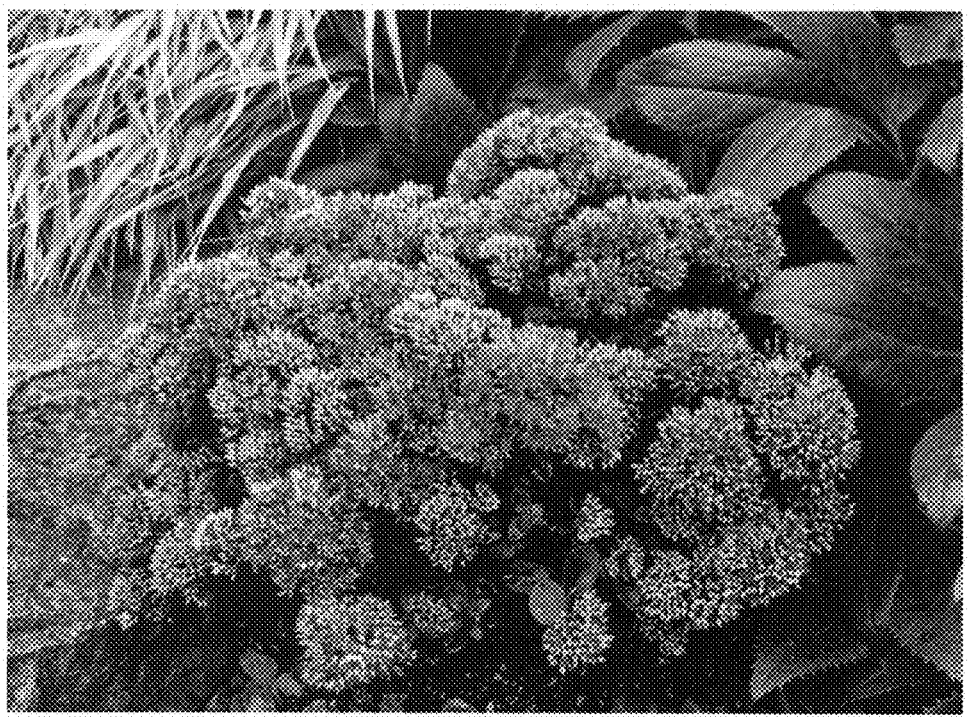

* * * * *